(12) United States Patent
Lee et al.

(10) Patent No.: US 10,427,991 B2
(45) Date of Patent: *Oct. 1, 2019

(54) CATALYST SYSTEM FOR OLEFIN OLIGOMERIZATION AND METHOD FOR OLEFIN OLIGOMERIZATION USING THE SAME

(71) Applicant: LG CHEM, LTD., Seoul (KR)

(72) Inventors: Yong Ho Lee, Daejeon (KR); Eun Ji Shin, Daejeon (KR); Jin Young Park, Daejeon (KR); Ki Soo Lee, Daejeon (KR); Seok Pil Sa, Daejeon (KR); Seul Ki Im, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/570,133

(22) PCT Filed: Jan. 11, 2016

(86) PCT No.: PCT/KR2016/000238
§ 371 (c)(1),
(2) Date: Oct. 27, 2017

(87) PCT Pub. No.: WO2016/186291
PCT Pub. Date: Nov. 24, 2016

(65) Prior Publication Data
US 2018/0127333 A1   May 10, 2018

(30) Foreign Application Priority Data
May 15, 2015  (KR) .................. 10-2015-0068301
Dec. 23, 2015  (KR) .................. 10-2015-0185319

(51) Int. Cl.
| | | |
|---|---|---|
| C07C 2/36 | (2006.01) | |
| C08F 10/00 | (2006.01) | |
| C07C 2/26 | (2006.01) | |
| C07C 11/02 | (2006.01) | |
| C08F 4/69 | (2006.01) | |
| C08F 10/02 | (2006.01) | |
| C07C 2/32 | (2006.01) | |
| B01J 21/02 | (2006.01) | |
| B01J 31/14 | (2006.01) | |
| B01J 31/18 | (2006.01) | |
| B01J 31/24 | (2006.01) | |
| B01J 31/34 | (2006.01) | |
| C07C 11/04 | (2006.01) | |
| B01J 31/16 | (2006.01) | |
| B01J 21/08 | (2006.01) | |

(52) U.S. Cl.
CPC ............ *C07C 2/36* (2013.01); *B01J 21/02* (2013.01); *B01J 31/143* (2013.01); *B01J 31/1608* (2013.01); *B01J 31/1616* (2013.01); *B01J 31/1805* (2013.01); *B01J 31/188* (2013.01); *B01J 31/24* (2013.01); *B01J 31/34* (2013.01); *C07C 2/26* (2013.01); *C07C 2/32* (2013.01); *C07C 11/02* (2013.01); *C07C 11/04* (2013.01); *C08F 4/69086* (2013.01); *C08F 10/00* (2013.01); *C08F 10/02* (2013.01); *B01J 21/08* (2013.01); *B01J 2231/20* (2013.01); *B01J 2531/62* (2013.01); *B01J 2540/52* (2013.01); *C07C 2521/08* (2013.01); *C07C 2523/26* (2013.01); *C07C 2531/14* (2013.01); *C07C 2531/18* (2013.01); *C07C 2531/22* (2013.01); *C07C 2531/24* (2013.01); *C07C 2531/34* (2013.01); *C08F 2410/03* (2013.01)

(58) Field of Classification Search
CPC combination set(s) only.
See application file for complete search history.

(56) References Cited

U.S. PATENT DOCUMENTS

| | | |
|---|---|---|
| 8,124,557 B2 | 2/2012 | Lee et al. |
| 9,988,469 B2 | 6/2018 | Song et al. |
| 2003/0166456 A1 | 9/2003 | Wass et al. |
| 2005/0020788 A1 | 1/2005 | Wass et al. |
| 2005/0228139 A1 | 10/2005 | Lee et al. |
| 2006/0128910 A1 | 6/2006 | Blann et al. |
| 2006/0173226 A1 | 8/2006 | Blann et al. |

(Continued)

FOREIGN PATENT DOCUMENTS

| | | |
|---|---|---|
| CN | 1727367 A | 2/2006 |
| CN | 101511851 A | 8/2009 |

(Continued)

OTHER PUBLICATIONS

Blann et al. "Ethylene tetramerisation:Subtle effects exhibited by N-substituted diphosphinoamine ligands", Journal of Catalysis, 2007, 249, 2, 244-249.

(Continued)

*Primary Examiner* — In Suk C Bullock
*Assistant Examiner* — Ali Z Fadhel
(74) *Attorney, Agent, or Firm* — Dentons US LLP

(57) ABSTRACT

The present invention relates to a catalyst system for olefin oligomerization and a method for olefin oligomerization, and more specifically, a catalyst system for olefin oligomerization and a method for olefin oligomerization that have more improved supporting efficiency due to a ligand compound capable of functioning as a tether to a support, and thus, exhibit high activity in the olefin oligomerization even with smaller amounts of catalyst composition and cocatalyst, thus enabling more efficient preparation of alpha-olefins.

11 Claims, No Drawings

(56) References Cited

U.S. PATENT DOCUMENTS

| | | |
|---|---|---|
| 2006/0211903 A1 | 9/2006 | Blann et al. |
| 2006/0229480 A1* | 10/2006 | Blann ............... B01J 31/14 585/535 |
| 2008/0027188 A1* | 1/2008 | Small ............... B01J 31/143 526/113 |
| 2010/0190939 A1 | 7/2010 | Fritz et al. |
| 2011/0172370 A1* | 7/2011 | Aliyev ............ B01J 31/1658 525/333.6 |
| 2011/0306739 A1 | 12/2011 | Carpentier et al. |
| 2012/0101321 A1 | 4/2012 | Brown et al. |
| 2012/0123078 A1 | 5/2012 | Lee et al. |
| 2012/0172645 A1 | 7/2012 | Sydora et al. |
| 2012/0310025 A1 | 12/2012 | Wang et al. |
| 2015/0011382 A1 | 1/2015 | Kwon et al. |
| 2015/0298110 A1 | 10/2015 | Cho et al. |
| 2015/0361118 A1 | 12/2015 | Lee et al. |
| 2016/0045906 A1 | 2/2016 | Sa et al. |
| 2016/0122371 A1 | 5/2016 | Lee et al. |
| 2016/0152742 A1 | 6/2016 | Lee et al. |
| 2016/0159828 A1 | 6/2016 | Lee et al. |
| 2016/0168281 A1 | 6/2016 | Lee et al. |
| 2016/0207946 A1 | 7/2016 | Shin et al. |
| 2016/0237187 A1 | 8/2016 | Hong et al. |
| 2016/0237188 A1 | 8/2016 | Hong et al. |
| 2016/0304637 A1 | 10/2016 | Lee et al. |
| 2017/0029346 A1 | 2/2017 | Lee et al. |
| 2018/0094085 A1 | 4/2018 | Park et al. |
| 2018/0127333 A1 | 5/2018 | Lee et al. |

FOREIGN PATENT DOCUMENTS

| | | |
|---|---|---|
| CN | 103270006 A | 8/2013 |
| CN | 103285926 A | 9/2013 |
| CN | 103429557 A | 12/2013 |
| CN | 104245711 A | 12/2014 |
| CN | 104254547 A | 12/2014 |
| CN | 104511311 A | 4/2015 |
| EP | 2955188 A1 | 12/2015 |
| EP | 3101039 A1 | 12/2016 |
| EP | 3243848 A1 | 11/2017 |
| JP | 2004-502527 A | 1/2004 |
| JP | 2006-516265 A | 6/2006 |
| JP | 2006-517528 A | 7/2006 |
| JP | 2011-518034 A | 6/2011 |
| JP | 2012-526175 A | 10/2012 |
| JP | 2013-515601 A | 5/2013 |
| JP | 2018-508355 A | 3/2018 |
| KR | 10-2003-0017616 A | 3/2003 |
| KR | 10-2008-0074339 A | 8/2008 |
| KR | 10-2010-0045636 A | 5/2010 |
| KR | 10-2011-0084303 A | 7/2011 |
| KR | 10-2012-0048468 A | 5/2012 |
| KR | 10-1241656 B1 | 3/2013 |
| KR | 10-2013-0142151 A | 12/2013 |
| KR | 10-2014-0063346 A | 5/2014 |
| KR | 10-2014-0126613 A | 10/2014 |
| KR | 10-2015-0037581 A | 4/2015 |
| KR | 10-2015-0057988 B1 | 5/2015 |
| KR | 10-2015-0058049 A | 5/2015 |
| KR | 10-2005-0098663 A | 10/2015 |
| KR | 10-2006-0002742 A | 1/2016 |
| WO | 2004-076502 A1 | 9/2004 |
| WO | 2014-175495 A | 10/2014 |
| WO | 2015046965 A1 | 4/2015 |
| WO | 2015/072811 A1 | 5/2015 |

OTHER PUBLICATIONS

Kuhlmann et al. "N-substituted diphosphinoamines:Toward rational ligand design for the efficient tetramerization of ethylene",Journal of Catalysis, 2007, vol. 245, pp. 279-284.

Carter et al. "High activity ethylene trimerisation catalysts based on diphosphine ligands", Chem. Commun., 2002, 858.

Yang et al. "Novel tandem catalytic system of b-diketonate zirconium/ two different cocatalysts for preparing branched polyethylene", Catalysis communications 10 (2009) 1427-1431.

Shao et al. "Preparation and Catalytic Performance of Silica-Supported Cr(acac)3/PNP for Ethylene Tetramerization", China Petroleum Processing and Petrochemical Technology, 2014, vol. 16, No. 1, pp. 45-51.

\* cited by examiner

CATALYST SYSTEM FOR OLEFIN OLIGOMERIZATION AND METHOD FOR OLEFIN OLIGOMERIZATION USING THE SAME

CROSS-REFERENCE TO RELATED APPLICATION(S)

This application is a National Stage Entry of International Application No. PCT/KR2016/000238 filed on Jan. 11, 2016, and claims the benefit of Korean Application No. 10-2015-0068301 filed on May 15, 2015, and Korean Application No. 10-2015-0185319 filed on Dec. 23, 2015, all of which are hereby incorporated by reference in their entirety for all purposes as if fully set forth herein.

TECHNICAL FIELD

The present invention relates to a catalyst system for olefin oligomerization and a method for olefin oligomerization, and more specifically, a catalyst system for olefin oligomerization and a method for olefin oligomerization that have more improved supporting efficiency due to a ligand compound capable of functioning as a tether to a support, and thus, exhibit high activity in the olefin oligomerization even with smaller amounts of catalyst composition and cocatalyst, thus enabling more efficient preparation of alpha-olefins.

BACKGROUND OF ART

Linear alpha-olefin is used as detergent, lubricant, plasticizer, etc., and particularly, is mainly used as comonomer for the control of the density of polymer when preparing Linear Low-Density Polyethylene(LLDPE).

In the conventional preparation process of LLDPE, copolymerization with comonomers such as alpha-olefins, for example, 1-hexene, 1-octene, etc. together with ethylene is made so as to form a branch on the polymer backbone to control the density.

Thus, there was a problem in that the cost of comonomers occupies a large part of a preparation cost so as to prepare LLDPE with high comonomer content. In order to overcome the problem, various methods have been attempted.

And, since alpha-olefins have different application field or market size according to the kind, a technology capable of simultaneously producing various olefins is very important, and recently, many studies on chromium catalyst technology for preparing 1-hexene, 1-octene or polyethylene with specific selectivity through ethylene oligomerization or ethylene polymerization are being progressed.

DETAILED DESCRIPTION OF THE INVENTION

Technical Problem

It is an object of the present invention to provide a catalyst system for olefin oligomerization that exhibits high catalytic activity in the olefin oligomerization, and has reduced leaching of catalyst material, and thus, can realize high catalytic activity and selectivity to linear alpha-olefin even if relatively small amount of a cocatalyst is introduced.

It is another object of the present invention to provide a method for olefin oligomerization using the catalyst system.

Technical Solution

The present invention provides a catalyst system for olefin oligomerization comprising: a ligand compound comprising two or more diphosphino moieties represented by the following Chemical Formula 1 in the molecule, and comprising a linker (L) connecting each moiety represented by the Chemical Formula 1: a chromium source; and a support where the ligand compound is supported.

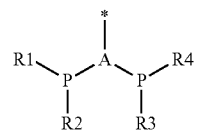

[Chemical Formula 1]

in the Chemical Formula 1,
P is a phosphorous atom,
A is nitrogen (N), arsenic (As), or antimony (Sb),
R1 to R4 are identical or different, and each independently, a C1-20 hydrocarbyl group, heterohydrocarbyl group, or hydrocarboheteryl group,
* is a part that binds with the linker(L) connecting two or more moieties.

Here, the unshared electron pair belonging to one or more diphosphino moieties among the two or more disphosphine moieties included in the ligand compound, may be coordinated to the chromium atom.

And, it may be preferable that among the two or more disphosphino moieties included in the ligand compound, one or more diphosphino moieties are tethered to the support.

And, it may be preferable that the ratio of the mole number of the chromium atom to the mole number of the ligand compound is 1 or less.

According to one embodiment of the invention, the ligand compound may be represented by the following Chemical Formula 2.

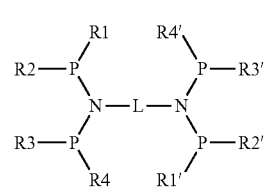

[Chemical Formula 2]

in the Chemical Formula 2,
P is a phosphorous atom,
N is a nitrogen atom, P is a nitrogen atom,
R1 to R4 and R1' to R4' are identical or different, and each independently, a C1-20 hydrocarbyl group, heterohydrocarbyl group, or hydrocarboheteryl group,
L is a C2-30 hydrocarbyl group or heterohydrocaryl group connecting the two or more disphosphino moieties.

And, according to one embodiment, L may be a linker with a carbon number of the shortest distance connecting the diphosphino moiety of 4 to 10, and may be a C2-20 aliphatic linking group, a C3-20 cycloaliphatic linking group, or a C6-20 aromatic linking group.

According to another embodiment of the invention, the chromium source may be one or more compounds selected from the group consisting of chromium(III) acetylacetonate, chromium(III) chloride tetrahydrofurane, chromium(III) 2-ethylhexanoate, chromium(III) acetate, chromium(III) butyrate, chromium(III) pentanoate, chromium(III) laurate, chromium(III) tris(2,2,6,6-tetramethyl-3,5-heptanedionate), and chromium(III) stearate.

And, the catalyst system for olefin oligomerization may further comprise a cocatalyst supported in the support.

Here, the cocatalyst may be one or more compounds selected from the group consisting of trimethyl aluminium, triethyl aluminium, triisopropyl aluminium, triisobutyl aluminum, ethylaluminum sesquichloride, diethylaluminum chloride, ethyl aluminium dichloride, methylaluminoxane, and modified methylaluminoxane.

Meanwhile, according to another aspect of the present invention, a method for olefin oligomerization comprising the step of progressing an oligomerization reaction of olefin-based monomers in the presence of the above described catalyst system to form alpha-olefin, is provided.

Here, it may be preferable that the olefin-based monomer is ethylene.

According to one embodiment of the invention, it may be preferable that the oligomerization reaction of the olefin-based monomers is conducted at a temperature of 5 to 200° C., and the oligomerization reaction of the olefin-based monomers is conducted at a pressure of 1 to 300 bar.

Advantageous Effects

The catalyst system for olefin oligomerization of the present invention may exhibit high activity even with a small amount of cocatalyst, because the cocatalyst may be uniformly distributed over the whole support.

And, one or more disphosphino moieties existing in the molecule of the ligand compound may be strongly tethered to the support, thus improving supporting efficiency, and reducing leaching of the catalyst composition. And, since it is easy to separate the catalyst from the liquid reactant and product, the production of other isomers may be reduced, and since the production of solid alpha-olefins occurs in the support, fouling, etc. that may occur on the surface of a reactor may be prevented.

DETAILED DESCRIPTION OF THE EMBODIMENTS

The terms used herein are only to explain specific embodiments, and are not intended to limit the present invention. A singular expression includes a plural expression thereof, unless it is expressly stated or obvious from the context that such is not intended. As used herein, the terms "comprise" or "have", etc. are intended to designate the existence of practiced characteristic, number, step, constructional element or combinations thereof, and they are not intended to preclude the possibility of existence or addition of one or more other characteristics, numbers, steps, constructional elements or combinations thereof.

Although various modifications can be made to the present invention and the present invention may have various forms, specific examples will be illustrated and explained in detail below. However, it should be understood that these are not intended to limit the present invention to specific disclosure, and that the present invention includes all the modifications, equivalents or replacements thereof without departing from the spirit and technical scope of the invention.

As used throughout the specification, 'oligomerization' means small degree of polymerization of olefins. For example, it is a generic term of multimerization including trimerization or tetramerization, etc. according to the repeat number of polymerized olefins, and particularly, in the specification, it means the selective preparation of 1-hexene and/or 1-octene that is used as the main comonomers of LLDPE, from ethylene.

And, throughout the specification, a hydrocarbyl group commonly designates hydrocarbon, and for example, it means an alkyl group, an aryl group, an alkenyl group, a cycloalkyl group, etc., and unless otherwise described, it includes both a linear chain and a branched chain, and both a substituted type and a non-substituted type.

And, throughout the specification, an alkylaryl group means an aryl group having one or more alkyl groups as substituents, and an arylalkyl group means an alkyl group having one or more aryl groups as substituents.

And, throughout the specification, a heteroatom means nitrogen, oxygen, sulfur, or phosphorous, and a heterohydrocarbyl group means a hydrocarbyl group including one or more heteroatoms. In case such a heterohydrocarbyl group is designated, it means that a connection point of functionalization is carbon, and in case a heteryl group is designated such as a 'hydrocarboheteryl group' or an organoheteryl group' etc., it means that a connection point of functionalization is a heteroatom.

Hereinafter, the present invention will be explained in more detail.

Although the existing many organic chromium-based catalysts could prepare alpha-olefin with high activity and selectivity through a liquid phase reaction using MAO or borate-based cocatalyst, in case it is supported on a support together with a cocatalyst, the reaction activity was extremely lowered in general.

However, the catalyst system according to one aspect of the present invention, even if supported on a support such as silica, etc., can prepare alpha-olefin with high activity and selectivity, and since it is a solid phase and thus can be easily separated from liquid phase reactants and products, the amount of isomers due to the adverse reactions or side reactions that may occur when the catalyst is not separated from the product can be reduced.

And, as such, since the catalyst system can be easily separated from the reaction system, by-products such as solid alpha-olefin due to the side reactions of homogeneous liquid phase reaction can be reduced.

And, since the olefin oligomerization may be progressed in the pores in the support, etc., even if solid alpha-olefin is produced, it can be fixed in the support and maintain the morphology, and thus, can be easily separated. Thus, it can be easily processed into low molecular PE product having high added value, and the problems of fouling, pipe blocking, etc. that may occur due to the remaining by-products in the reactor, can be prevented.

Furthermore, leaching of the catalyst composition can be reduced, and thus, the amount of loss can be reduced when preparing a catalyst, which is favorable in economical terms.

The catalyst system for olefin oligomerization according to one aspect of the present invention comprises a ligand compound comprising two or more diphosphino moieties represented by the following Chemical Formula 1 in the molecule, and comprising a linker(L) connecting each moiety represented by the Chemical Formula 1:

a chromium source; and a support where the ligand compound is supported.

[Chemical Formula 1]

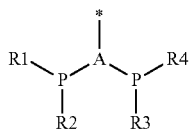

in the Chemical Formula 1,
P is a phosphorous atom,
A is nitrogen (N), arsenic (As), or antimony (Sb),
R1 to R4 are identical or different, and each independently, a C1-20 hydrocarbyl group, heterohydrocarbyl group, or hydrocarboheteryl group,
* is a part that binds with the linker(L) connecting two or more moieties.

The ligand compound comprises diphoshpino moieties in the molecule, and due to the abundant electron density of the A atom and the linker, it can provide unshared electron pair to a ligand such as chromium, etc.

Due to such structural characteristics, the electrical, steric properties of the whole ligand compound may vary, and the bonding between the ligand and the chromium atom may be modified, and thus, the structure of the catalyst may be more stabilized, and compared to the reaction mechanism by the existing metallacycloheptane or metallacyclononane, a transition state energy, i.e., the activation energy of reaction may be changed to form alpha-olefins with higher activity and selectivity.

For example, the ligand compound may be represented by the following Chemical Formula 2.

[Chemical Formula 2]

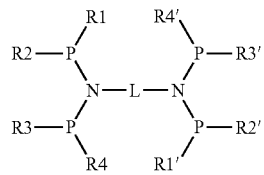

in the Chemical Formula 2,
P is a phosphorous atom,
N is a nitrogen atom, P is a nitrogen atom,
R1 to R4 and R1' to R4' are identical or different, and each independently, a C1-20 hydrocarbyl group, heterohydrocarbyl group, or hydrocarboheteryl group,
L is a C2-30 hydrocarbyl group or heterohydrocaryl group connecting the two or more disphosphine moieties.

More specifically, in the Chemical Formulas 1 and 2, R1 to R4 and R1' to R4' may be, for example, a C6-20 aryl group, hetero aryl group or arylheteryl group; or a C7-20 alkylaryl group, heteroalkylaryl group, alkylheteroaryl group, or alkylarylheteryl group.

And, the linker(L) may be a hydrocaryl group, a heterohydrocarbyl group, or a hydrocarbylheteryl group of various structures, and the number of atoms of the shortest distance between diphosphino moieties may be 2 to 30. Specifically, for example, it may be a C2-20 aliphatic linker, a C2-20 heteroaliphatic linker, a C3-20 cycloaliphatic linker, a C3-20 heteroaliphatic linker, a C6-20 aromatic linker, or a C6-20 heteroaromatic linker, and the structure is not specifically limited.

And, if two or more groups selected from the above linkers are decided as main chains, the main chains of the linker may have substituents of various structures.

Non-limiting examples of the above described linker may include those having the following structural formulas. In the examples below, the diphosphino moiety represented by the Chemical Formula 1 is indicated as [A], [A'], or [A"] for convenience, and each diphosphino moiety may be the same or different.

In case plural diphosphino moieties are connected through 2 or 3 carbon atoms:

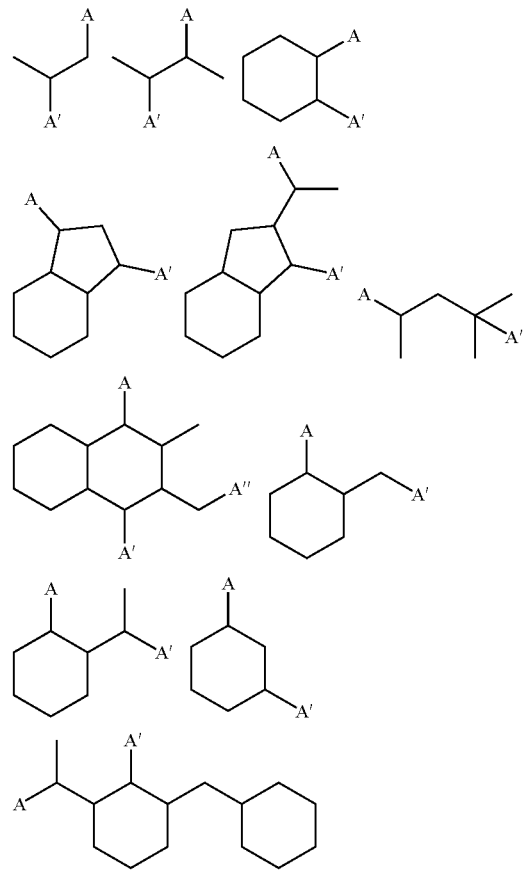

(ii) In case plural diphosphino moieties are connected through 4 carbon atoms:

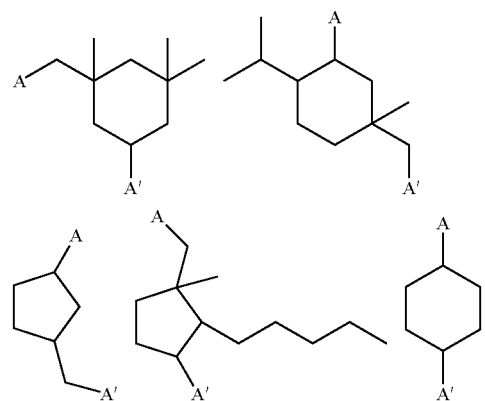

(iii) In case plural diphosphino moieties are connected through 5 carbon atoms:

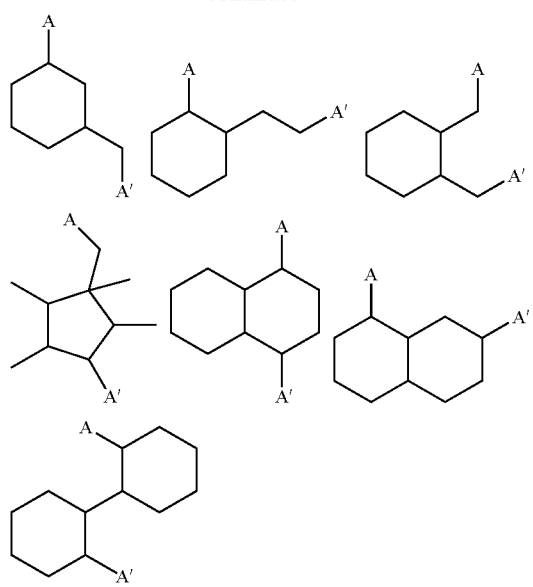

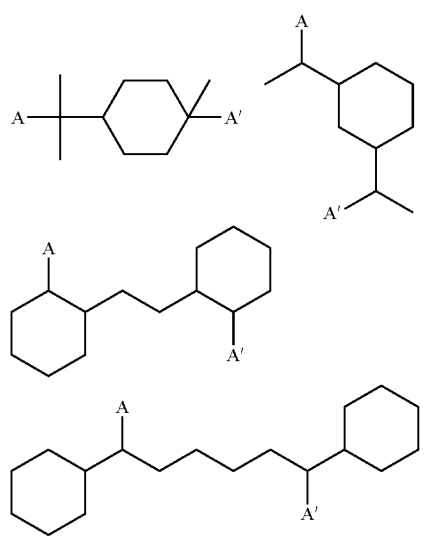

More specifically, for example, the linker(L) may be a first linker, a second linker or a third linker explained below.

The first linker may have 4 carbon number of the shortest distance between diphosphino moieties, it may be a C1-20 aliphatic linker, a C3-20 cyclialiphatic linker, and a C6-20 aromatic linker, and it may have the following structural formulas.

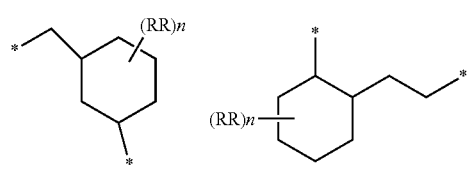

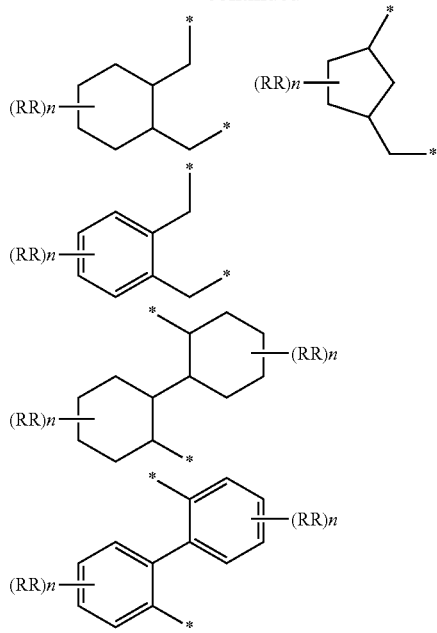

In the Structural formulas, * is a part connected with the diphosphino moiety represented by the Chemical Formula 1, RR's are each independently a C1-5 alkyl group, n is the number of substitution on each ring, and may vary according to the number of substitution within an integer range of 1 to 4, and plural RR's bound to one ring may be the same or different.

In this case, the ligand compound may have the following structural formulas, for example:

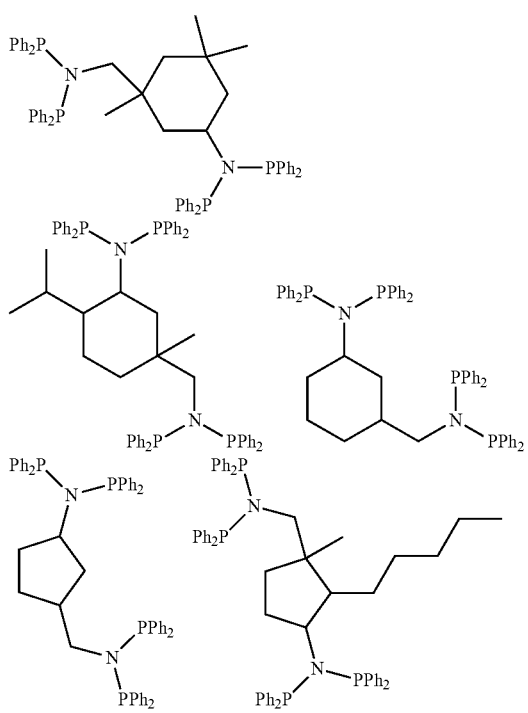

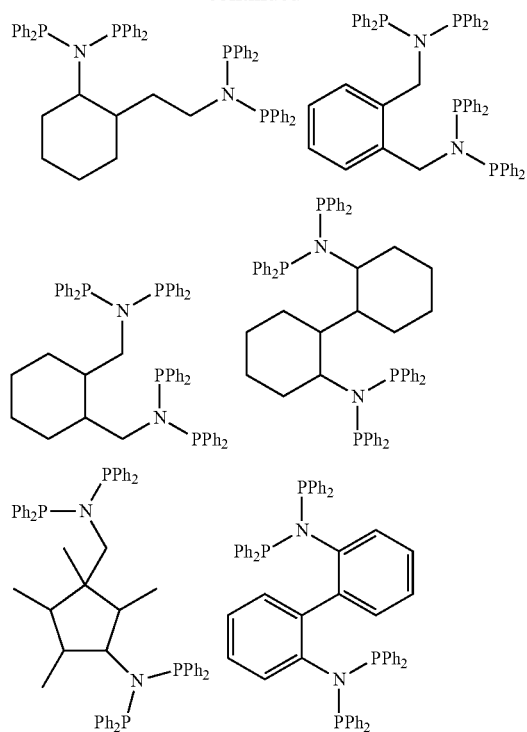

And, the second linker may have 5 to 8 carbon number of the shortest distance between diphosphino moieties, may consist of a C5-20 aliphatic linker or consist of a linker including a C1-20 aliphatic compound and a C6-20 aromatic compound connected with each other, and at least one end of the linker may be unsubstituted or substituted with a C6-20 aryl group.

Specifically, the second linker may have the following structural formulas.

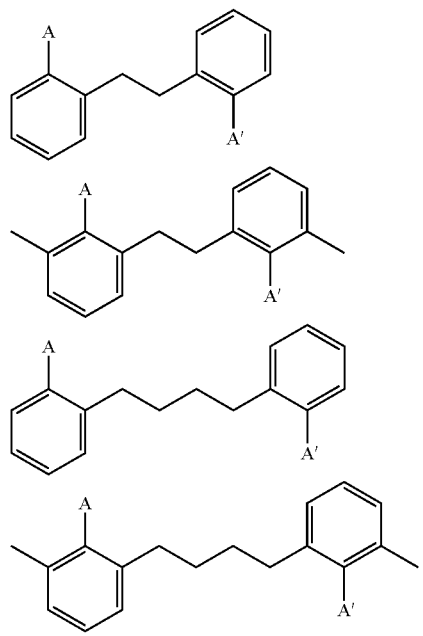

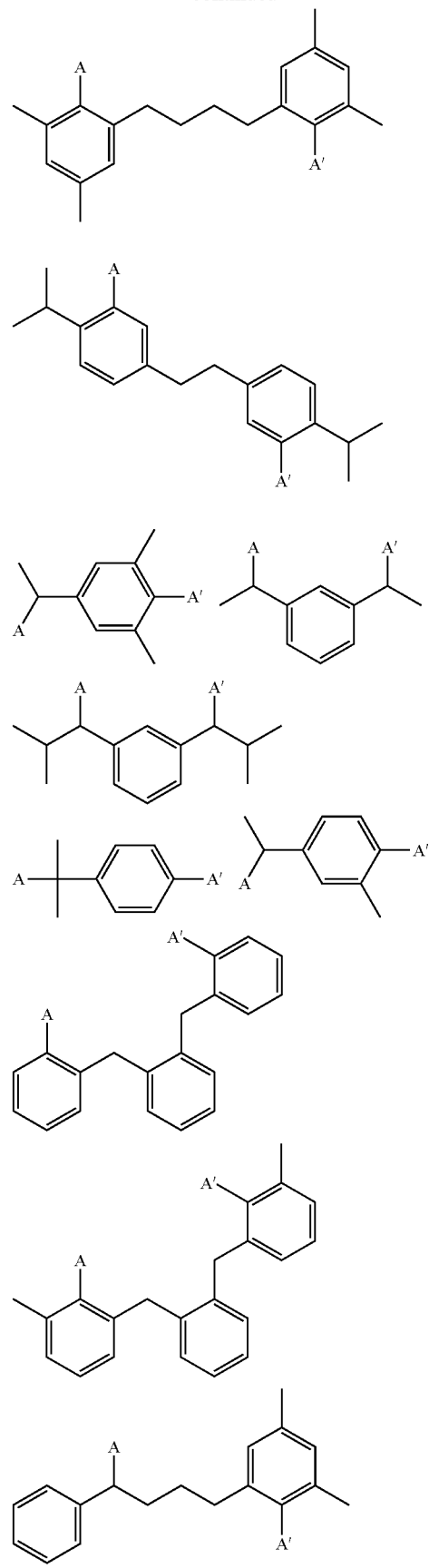

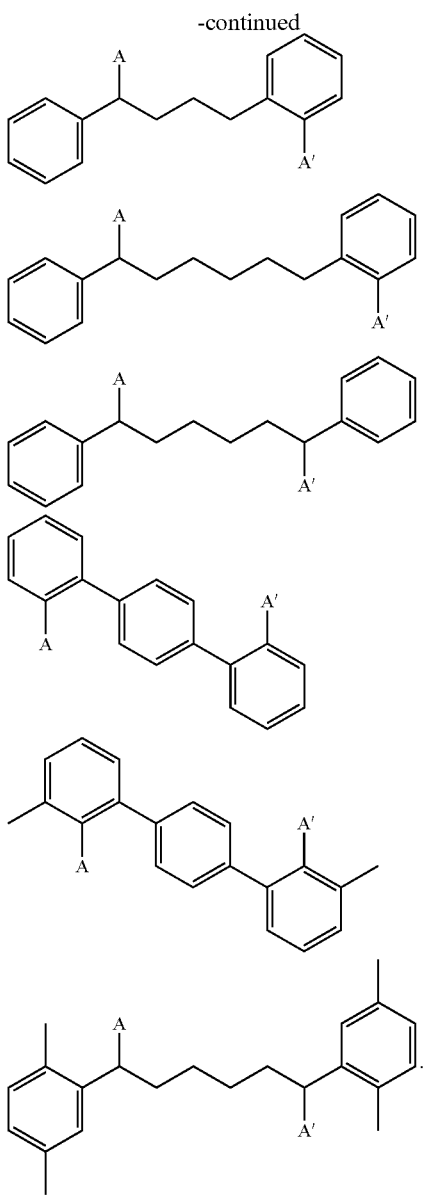

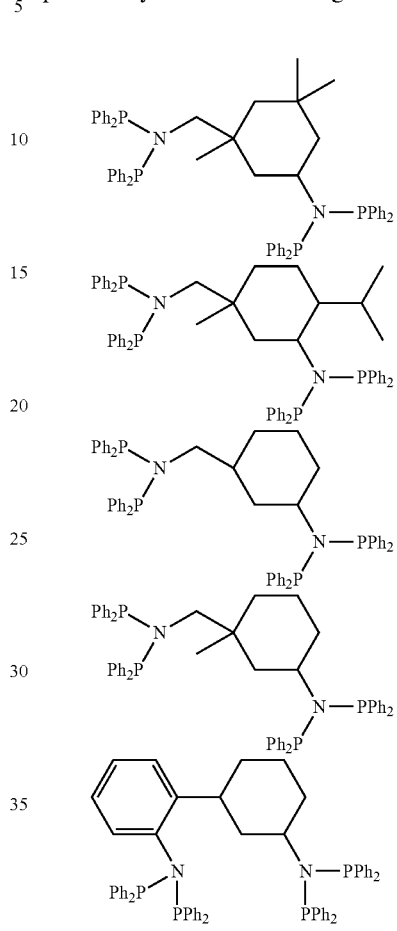

aryl group, a C7-18 alkyaryl group, a C7-18 arylalkyl group, or a C7-18 alkoxyaryl group.

In this case, representative examples of the ligand compound may have the following structural formulas.

Due to the above structure of a linker(L), the activity of supported catalyst may be further improved, and it may be favorable in terms of selectivity to linear alpha-olefins.

According to one embodiment of the invention, the compound may exist in the form of an organochromium compound wherein the unshared electron pairs belonging to one or more diphosphino moieties among the two or more disphosphino moieties included in the ligand compound, are coordinated to the chromium atom.

And, it may be preferable that among the two or more disphosphino moieties included in the ligand compound, one or more diphosphino moieties are tethered to the support.

Namely, among the two or more diphosphino moieties included in the ligand compound, one or more diphosphino moieties may function as a tethering group, and one or more of the remaining diphosphino moieties may be coordinated to chromium and function as an active site of the reaction.

Specifically, the phosphorous atoms of the diphosphino moiety functioning as a tethering group act as an electron donor providing unshared electron pair, and metal or nonmetal atom included in the support, for example, silicon or aluminum acts as an electron acceptor, thereby forming a Lewis acid-base bond, and thus, the ligand compound and the support may be fixed with a strong binding force.

And, the third linker may have 4 to 23 carbon number of the shortest distance between diphosphino moieties, and may be represented by the following Chemical Formula 3.

[Chemical Formula 3]

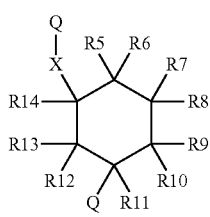

In the Chemical Formula 3,

Q means a diphosphino moiety represented by the Chemical Formula 1,

X is a C1-20 alkylene or a C6-14 arylene, and

R5 to R 14 are the same or different, and each independently, a C1-20 alkyl group, a C2-20 alkenyl group, a C6-14

By such tethering, compared to other supported catalysts, supporting force may be improved, and thus, supporting efficiency may be excellent, and leaving of the catalyst components from the support may be reduced during the reaction or separation.

In this respect, it may be more preferable that each linker(L) comprises an aliphatic linking group with relatively flexible bond so as to smoothly act as a tethering group and an active site. For example, in case the linking group does not comprise an aliphatic compound and consists only of cycloaliphatic or aromatic compound, interactions may be extremely limited due to the stiff bond, and thus, catalytic activity may be significantly lowered, and selectivity to linear alpha-olefins may be also lowered.

And, the ligand compound may be included in the amount of about 0.5 to about 20 parts by weight, preferably about 1 to about 15 parts by weight, more preferably about 1 to about 10 parts by weight, based on 100 parts by weight of the support, on the basis of the weight of the chromium-coordinated state.

According to one embodiment of the invention, the ratio of the mole number of the chromium atoms to the mole number of the ligand compound may be 1 or less, and preferably the ratio of ligand:chromium may be 1:1 to 10:1, more preferably 1:1 to 5:1. Namely, it is preferable that the mole number is determined within the above range, so that among the diphosphino moieties existing in the ligand compound, at least one may be tethered to the support.

The support has a specific surface area where catalyst components can be sufficiently supported, and common supports containing a lot of pores inside may be used so that the olefin oligomerization may smoothly occur.

Namely, as the support, metal or non-metal, salts thereof or oxides thereof, commonly used in supported catalysts, may be used without specific limitations, and more specifically, silica, alumina, silica-alumina, silica-magnesia, etc. may be applied, but the present invention is not limited thereto. Such a support may be dried at high temperature, and in general, may comprise oxide, carbonate, sulfate or nitrate of metal, such as sodium oxide, potassium carbonate, barium sulfate, magnesium nitrate, etc.

And, although it is preferable that the surface of the support less comprises hydroxy groups, it is impossible to remove all the hydroxy groups, and thus, it may be important to control the drying conditions, etc. when preparing the support, thus controlling the amount of hydroxy groups. For example, the hydroxy groups may be about 10 mmol/g or less, preferably about 1 mmol/g or less, more preferably about 0.5 mmol/g or less, based on the mass of the support. And, in order to reduce the side reactions of a few hydroxy groups remaining after drying, supports from which hydroxy groups have been selectively removed while conserving siloxane groups having high support reactivity, may be used.

In the catalyst system, the source of chromium may be organic or inorganic chromium compound with a chromium oxidation state of 0 to 6, for example, a chromium metal, or a compound wherein any organic or inorganic radicals are bonded chromium. Here, the organic radical may be C1-20 alkyl, alkoxy, ester, ketone, amido, carboxylate radicals, etc., and the inorganic radical may be halide, sulfate, oxide, etc.

Specifically, for example, the chromium source may be one or more compounds selected from the group consisting of chromium(III) acetylacetonate, chromium(III) chloride tetrahydrofurane, chromium(III) 2-ethylhexanoate, chromium(III) acetate, chromium(III) butyrate, chromium(III) pentanoate, chromium(III) laurate, chromium(III) tris(2,2,6,6-tetramethyl-3,5-heptanedionate), and chromium(III) stearate.

According to another embodiment of the invention, the above explained catalyst system may further comprise a cocatalyst supported on the support.

And, preferably, the cocatalyst is an organometal compound comprising Group 13 metal, and those commonly used when polymerizing olefins in the presence of transition metal catalysts may be used without specific limitations.

For example, the cocatalyst may be one or more compounds selected from the group consisting of the compounds represented by the following Chemical Formulas 4 to 6:

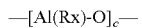   [Chemical Formula 4]

In the Chemical Formula 4, Al is aluminum,

Rx may be identical or different, and each independently, halogen, C1-20 hydrocarbyl radical, or C1-20 hydrocarbyl radical substituted with halogen, and c is an integer of 2 or more,

   [Chemical Formula 5]

In the Chemical Formula 5, D is aluminum or boron, and Ry C1-20 hydrocarbyl radical, or C1-20 hydrocarbyl radical substituted with halogen,

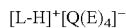   [Chemical Formula 6]

In the Chemical Formula 6,

L is neutral Lewis base, [L-H]$^+$ is Bronsted acid, Q is boron or aluminum in the +3 oxidation state, E's are independently a C6-20 aryl group or a C1-20 alkyl group, at least one hydrogen of which is unsubstituted or substituted with halogen, a C1-20 hydrocarbyl, an alkoxy functional group, or a phenoxy functional group.

According to one embodiment, the compound represented by the Chemical Formula 4 may be alkylaluminoxane such as methylaluminoxane, ethylaluminoxane, isobutylaluminoxane, butylaluminoxane, etc.

And, according to one embodiment, the compound represented by the Chemical Formula 5 may be trimethylaluminum, triethylaluminum, triisobutylaluminum, tripropylaluminum, tributylaluminum, dimethylchloroaluminum, dimethylisobutylaluminum, dimethylethylaluminum, diethylchloroaluminum, triisopropylaluminum, tri-s-butylaluminum, tricyclopentylaluminum, tripentylaluminum, triisopentylaluminum, trihexylaluminum, ethyldimethylaluminum, methyldiethylaluminum, triphenylaluminum, tri-p-tollylaluminum, dimethylaluminum mexhoxide, dimethylaluminum ethoxide, trimethylboron, triethylboron, triisobutylboron, tripropylboron, tributylboron, etc.

And, according to one embodiment, the compound represented by the Chemical Formula 6 may be triethylammoniumtetraphenylboron, tributylammoniumtetraphenylboron, trimethylammoniumtetraphenylboron, tripropylammoniumtetraphenylboron, trimethylammoniumtetra(p-tollyl)boron, tripropylammoniumtetra(p-tollyl)boron, triethylammoniumtetra(o,p-dimethylphenyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylaniliniumtetraphenylboron, N,N-diethylaniliniumtetraphenylboron, N,N-diethylaniliniumtetrapentafluorophenylboron, diethylammoniumtetrapentafluorophenylboron, triphenylphosphoniumtetraphenylboron, trimethylphosphoniumtetraphenylboron, triethylammoniumtetraphenyl aluminum, tributylammoniumtetraphenylaluminum, trimethylammoniumtetraphenylaluminum, tripropylammoniumtetraphenylaluminum, trimethylammoniumtetra(p-tollyl)aluminum, tripropylammoniumtetra(p-tollyl)aluminum, triethylammoniumtetra(o,p-dimethylphenyl)aluminum, tributylammoniumtetra(p-trifluoromethylphenyl)aluminum, trimethyl ammoniumtetra(p-trifluoromethylphenyl)aluminum, tributylammoniumtetrapentafluorophenylaluminum, N,N-diethylaniliniumtetraphenylaluminum, N,N-diethylaniliniumtetrapentafluorophenylaluminum, diethylammoniumtetrapentafluorophenylaluminum, triphenylphosphoniumtetraphenylaluminum, trimethylphosphoniumtetraphenylaluminum, triphenylcarboniumtetraphenylboron, triphenylcarboniumtetraphenylaluminum, triphenylcarboniumtetra(p-trifluoromethylphenyl)boron, triphenylcarboniumtetrapentafluorophenylboron, and the like.

And, as non-limiting examples, the cocatalyst may be an organoaluminium compound, an organiboron compound, an organomagnesium compound, an organozinc compound, an organolithium compound, or a mixture thereof. According to one embodiment, the cocatalyst may be preferably an organoaluminium compound, and more preferably, it may be one or more compounds selected form the group consisting of trimethyl aluminium, triethyl aluminium, triisopropyl aluminium, triisobutyl aluminum, ethylaluminum sesquichloride, diethylaluminum chloride, ethyl aluminium dichloride, methylaluminoxane, and modified methylaluminoxane.

In case both a ligand compound and a cocatalyst are supported, although the content of each component is not specifically limited, the mole ratio of the ligand compound and the cocatalyst may be about 1:5 to about 1:1,000, preferably about 1:10 to about 1:250.

And, based on 100 parts by weight of the support, the cocatalyst may be included in the content of about 1 to about 1,000 parts by weight, preferably about 10 to about 100 parts by weight, more preferably about 40 to about 150 parts by weight.

The chromium-coordinated ligand compound and the cocatalyst may be supported on one support with a uniform composition, or may be respectively supported on different supports.

And, the supporting method is not specifically limited, and the cocatalyst may be first supported on a support, and then, the chromium-coordinated ligand compound may be supported. In this case, the amount of the cocatalyst to be finally supported may be divided into two, and the cocatalyst may be supported two times.

The supporting of the cocatalyst and the ligand compound may be progressed at a temperature of about 20 to 120° C. for about 1 to about 20 hours.

Specifically, it may comprise the steps of contacting a cocatalyst with a support to support the cocatalyst inside of and on the surface of the support; and adding a mixture comprising a ligand compound and a chromium source to the cocatalyst-supported support, thus supporting.

And, in the step of supporting the cocatalyst, the temperature at the time of the introduction of the cocatalyst may vary, and the cocatalyst may be introduced dividedly one or more times, wherein each introduction temperature may be sequentially lowered from the initial introduction temperature, and for example, it may be progressed under temperature conditions of being sequentially lowered from about −50° C. to about 150° C.

As such, if the cocatalyst is introduced dividedly one or more times, and the cocatalyst is contacted with a support while gradually lowering the temperature at each introduction step, the cocatalyst may be uniformly supported outside and inside of the support, and thus, the amount of loss of the cocatalyst may be reduced, and finally, even if a small amount of cocatalyst is used, high activity may be maintained during olefin oligomerization.

Meanwhile, according to another aspect of the present invention, a method for olefin oligomerization comprising the step of progressing an oligomerization reaction of olefin-based monomers in the presence of the above explained catalyst system to form alpha-olefin, is provided.

Here, it may be preferable that the olefin-based monomer is ethylene.

In general, the olefin oligomerization may be conducted using a common equipment and contact technology. As non-limiting examples, olefin oligomerization may be conducted as a homogeneous liquid phase reaction in the presence or absence of inert solvents, slurry reaction wherein a part or the whole of the catalyst system is not dissolved, or a bulk phase reaction wherein product alpha-olefin or polyethylene acts as a main medium, or gas phase reaction.

However, in the homogeneous liquid phase reaction, solid alpha-olefins are necessarily produced as by-products, and such solid alpha-olefins remain in heterogeneous forms in the liquid phase of the reaction system, and thus, may lower the efficiency of oligomerization, lower selectivity to linear alpha-olefins, and generate side effects such as fouling, etc.

However, in the present invention, since oligomerization is conducted in the pores, etc. in the supported catalyst, catalyst stability is very high, and even if solid alpha-olefins are generated, morphology of oligomerization may be maintained.

And, since one or more of diphosphino moieties included in the ligand compound may be strongly tethered to a support and reduce leaching of catalytically active components, the efficiency of the reaction may be increased and the content of impurities may be reduced, as explained above.

And, the olefin oligomerization may be conducted under an inert solvent. As non-limiting examples, the inert solvent may be benzene, toluene, xylene, cumene, chlorobenzene, dichlorobenzene, heptanes, cyclohexane, methylcyclohexane, methylcyclopentane, n-hexane, 1-hexene, 1-octene, etc.

And, the olefin oligomerization may be conducted at a temperature of about 0 to about 200° C., or about 0 to about 150° C., or about 30 to about 100° C., or about 50 to about 100° C. And, the reaction may be conducted under pressure of about 1 to about 300 bar, or about 2 to about 150 bar.

Hereinafter, the actions and effects of the present invention will be explained in detail with reference to specific examples of the invention. However, these examples are presented only as the illustrations of the invention, and the scope of the present invention is not limited thereby.

Example

Preparation of a Support

Silica (SP 952X, Grace Davison Company) was vacuum dried at a temperature of 200° C. for 12 hours to prepare a support, which is stored in a glove box of argon atmosphere.

Preparation of a Ligand Compound

Preparation Example 1

Preparation of

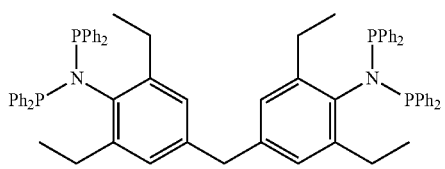

Using a flask, under argon, 5 mmol of 4,4'-methylenebis(2,6-diethylaniline) and triethyl amine (4 to 10 amine equivalents) were dissolved in 80 ml of dichloromethane.

While the flask was soaked in a water bath, 20 mmol of chlorodiphenylphosphine (4 equivalents to amine) was slowly added dropwise, and the solution was stirred overnight.

Vacuum was taken to remove the solvent, and then, THF was put, the solution was sufficiently stirred, and triethylammonium chloride salt was removed through an air-free glass filter. The solvent was removed in the filtrate to obtain a ligand compound represented by the above Structural Formula.

Preparation Example 2

Preparation of

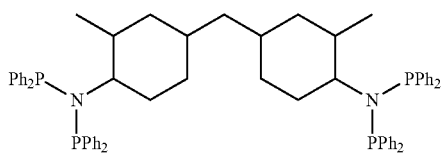

A ligand compound was prepared by the same method as Preparation Example 1, except that 4,4'-methylenebis(2-methylcyclohexaamine) was used instead of 4,4'-methylenebis(2,6-diethylaniline).

Preparation Example 3

Preparation of

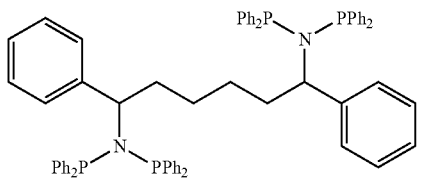

A ligand compound was prepared by the same method as Preparation Example 1, except that 1,6-diphenylhexane-1,6-diamine was used instead of 4,4'-methylenebis(2,6-diethylaniline).

Comparative Preparation Example 1

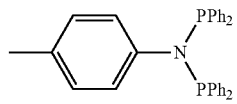

A ligand compound was prepared by the same method as Preparation Example 1, except that para-toluidine was used instead of 4,4'-methylenebis(2,6-diethylaniline), and chlorodiphenylphosphine was used in 2 equivalents to amine.

Comparative Preparation Example 2

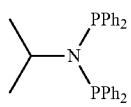

A ligand compound was prepared by the same method as Comparative Preparation Example 1, except that propane-2-amine was used instead of para-toluidine.

Preparation of a Supported Catalyst System

Examples 1 to 3

To the ligand compounds prepared in Preparation Examples 1 to 3, trivalent chromium acetate (224.5 mg, 0.7 mmol) prepared as a chromium source was put into the flask such that the mole ratio became 1:1, and 65 ml of toluene was added.

7 g of the above prepared support was put into a glass reactor of 40° C., and a methylaluminoxane (MAO) solution containing 77 mmol of aluminium was added and supported.

Here, the catalyst composition comprising a ligand compound and a chromium source prepared above was put, stirred and reacted for 2 hours, and then, the stirring was stopped and the filtrate was removed.

It was washed with a sufficient amount of toluene, 100 ml of hexane was put and stirred to prepare a slurry solution, which was transferred to an argon substituted flask, followed by the removal of a filtrate and vacuum drying, thus obtaining a supported catalyst in the form of solid powder.

Reference Example 1

A supported catalyst in the form of solid powder was obtained by the same method as Example 2, except that the mole number of the chromium to the mole number of ligand compound was adjusted to 2:1.

Comparative Examples 1 and 2

Supported catalysts were prepared by the same method as Examples, except that the ligand compounds prepared in Comparative Preparation Examples 1 and 2 were used, and 0.35 mmol of trivalent chromium acetate was used as a chromium source.

Preparation of Ethylene Oligomer

[Examples 1 to 3, Reference Example 1, and Comparative Examples 1 and 2]

An oligomerization reaction was conducted in a metal alloy reactor with a capacity of 600 ml, which is equipped with a mechanical stirrer, of which temperature can be controlled, and which can be operated under high pressure.

Each 30 mg of the supported catalysts prepared in Examples 1 to 3, Reference Example 1 and Comparative Examples 1 and 2 were measured in a dry box and put in a glass bottle. It was sealed with a rubber diaphragm, taken out of the dry box, and introduced into a reactor.

Into the reactor, 400 ml of hexane containing 1.0 mmol of triethylaluminium and the prepared supported catalyst were introduced so as not to contact the air, and an oligomerization reaction was conducted for 1 hour while continuously introducing gas phase ethylene monomers at 80° C. under pressure of 30 bar.

Thereafter, the stirring was stopped, and unreacted ethylene was removed by ventilation, thus finishing the reaction.

And, a small amount of the liquid part inside the reactor was taken and quenched with water, and the organic layer was filtered with a PTFE syringe filter to conduct GC analysis.

To the remaining reaction solution, 409 ml of ethanol/HCl (10 vol %) was added, and the solution was stirred and then filtered to obtain polymer, which was dried in a vacuum oven of 60° C. for 12 hours or more, and then, the weight was measured.

Comparative Example 3

A reaction was progressed with a cocatalyst composition and reaction conditions identical to Example 1, except that the ligand compound prepared in Preparation Example 1 was not supported on a support, and the catalyst and the cocatalyst were respectively dissolved in a solution state, thus progressing a homogeneous liquid phase reaction.

The results are summarized in the following Table 1.

TABLE 1

| | Al/Cr (the ratio of mole number) | Catalyst State | Activity (kg/molCr/Hr) | 1-C6 (g) | 1-C8 (g) | oligomer (g) |
|---|---|---|---|---|---|---|
| Example 1 | 220 | Supported | 30,700 | 6.38 | 0.50 | 8.37 |
| Example 2 | 220 | Supported | 41,600 | 14.29 | 1.27 | 19.36 |
| Example 3 | 220 | Supported | 42,100 | 19.20 | 1.78 | 26.33 |
| Reference Example 1 | 220 | Supported | 42,400 | 13.38 | 1.17 | 18.06 |
| Comparative Example 1 | 220 | Supported | 3,100 | 0.50 | 0.19 | 1.26 |
| Comparative Example 2 | 220 | Supported | 5,300 | 1.65 | 0.41 | 3.28 |
| Comparative Example 3 | 220 | Liquid phase | 533 | 0.12 | 0.03 | 0.25 |

Referring to Table 1, it is confirmed that, compared to Comparative Examples 1 and 2 wherein ligand compounds comprising only one diphosphino moiety are supported on a support, Examples 1 to 3 wherein ligand compounds comprising two or more diphosphino moieties are supported on a support are excellent in terms of catalytic activity or oligomer selectivity.

Specifically, in terms of catalytic activity, it is confirmed that Examples and Reference Example exhibit about 10 times or more higher activities than Comparative Examples. Particularly, Reference Example also exhibits very high activity, which is thought to result from two catalyst active sites in one ligand molecule due to the use of 2 moles of chromium to the ligand compound.

And, although Examples used relatively smaller amount of chromium compared to Reference Example, they exhibited activities equivalent to or more excellent than Reference Example, which is thought to result from the tethering function of the diphosphino moieties included in the ligand compound. More specifically, it is thought that in the ligand compound having two or more diphosphino moieties, only one diphosphino moiety is coordinated to the chromium atom, and the remaining one functions as a tether to a support, and thus, binding force with a support is improved, and leaving of catalytically active components is reduced during the washing process conducted for the preparation of a supported catalyst.

To the contrary, it is confirmed that although Comparative Examples 1 and 2 use supported catalyst forms, tethering effects are insignificant, and the catalytic activities are as low as about 10% of Examples.

Meanwhile, comparing the case of using a supported catalyst system and the case of using a liquid phase catalyst system for the same composition, it is confirmed that in the liquid phase catalyst system (Comparative Example 3), catalytic activity was very lowered to about 1% of Example. It is thought to result from the use of only 220 equivalents of cocatalyst, although in the case of a liquid phase catalyst system, in general, cocatalyst (based on aluminium equivalent in the cocatalyst) should be 600 equivalents or more, preferably 900 to 1500 equivalents to the mole number of chromium so as to secure activity to some extent.

That is, it can be seen that in case a supported catalyst system is used, even if relatively smaller amount of cocatalyst is used compared to common liquid phase catalyst system, catalytic activity is very excellent, and selectivity to linear alpha-olefin is also high. It is thought to result from the supporting of the cocatalyst and catalytically active components (ligand compound-chromium complex) on one support together, and the resulting close distance, and uniform distribution of the cocatalyst inside and outside of the support.

The invention claimed is:

1. A catalyst system for olefin oligomerization comprising:

at least one ligand compound represented by the following Chemical Formulas:

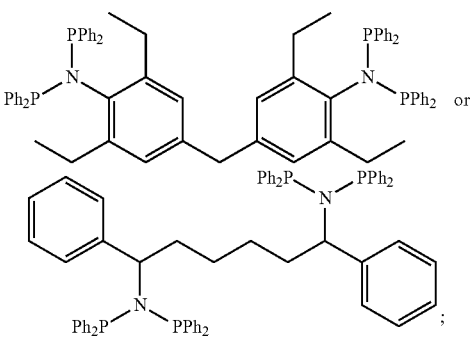

a chromium source; and
a support wherein the ligand compound is supported on the support.

2. The catalyst system for olefin oligomerization according to claim 1, wherein the unshared electron pair belonging to one or two diphosphino moieties among the two diphosphino moieties included in the ligand compound, is coordinated to the chromium atom.

3. The catalyst system for olefin oligomerization according to claim 1, wherein among the two disphosphino moieties included in the ligand compound, one or two diphosphino moieties are tethered to the support.

4. The catalyst system for olefin oligomerization according to claim 1, wherein the ratio of the mole number of the chromium atom to the mole number of the ligand compound is 1 or less.

5. The catalyst system for olefin oligomerization according to claim 1, wherein the chromium source is one or more compounds selected from the group consisting of chromium (III) acetylacetonate, chromium(III) chloride tetrahydrofurane, chromium(III) 2-ethylhexanoate, chromium(III) acetate, chromium(III) butyrate, chromium(III) pentanoate, chromium(III) laurate, chromium(III) tris(2,2,6,6-tetramethyl-3,5-heptanedionate), and chromium(III) stearate.

6. The catalyst system for olefin oligomerization according to claim 1, further comprising a cocatalyst supported on the support.

7. The catalyst system for olefin oligomerization according to claim 6, wherein the cocatalyst is one or more compounds selected from the group consisting of trimethyl aluminium, triethyl aluminium, triisopropyl aluminium, triisobutyl aluminum, ethylaluminum sesquichloride, diethylaluminum chloride, ethyl aluminium dichloride, methylaluminoxane, and modified methylaluminoxane.

8. A method for olefin oligomerization comprising: oligomerizing olefinic monomers in the presence of the catalyst system according to claim 1 to form an alpha-olefin oligomer.

9. The method for olefin oligomerization according to claim 8, wherein the olefinic monomer is ethylene.

10. The method for olefin oligomerization according to claim 8, wherein the oligomerizing is conducted at a temperature of 5° C. to 200° C.

11. The method for olefin oligomerization according to claim 8, wherein the oligomerizing is conducted at a pressure of 1 bar to 300 bar.

* * * * *